United States Patent [19]

Opel

[11] Patent Number: 4,579,868
[45] Date of Patent: Apr. 1, 1986

[54] SURFACE ANALGESIC AND ANTIPHLOGISTIC

[76] Inventor: Helmut Opel, Hudtwalckerstr. 2-8, 2000 Hamburg 60, Fed. Rep. of Germany

[21] Appl. No.: 671,418

[22] Filed: Nov. 14, 1984

[30] Foreign Application Priority Data

Nov. 17, 1983 [DE] Fed. Rep. of Germany ....... 3341569
Oct. 30, 1984 [DE] Fed. Rep. of Germany ....... 3439577

[51] Int. Cl.⁴ ...................... A61K 31/23; A61K 47/00
[52] U.S. Cl. .................................... 514/552; 514/762
[58] Field of Search ................................ 514/552, 762

[56] References Cited

U.S. PATENT DOCUMENTS 4,263,313 4/1981 Eckert et al. ...................... 424/230
4,514,386 4/1985 Yamahira ............................. 424/81

*Primary Examiner*—Stanley J. Friedman
*Attorney, Agent, or Firm*—Cushman, Darby & Cushman

[57] ABSTRACT

The invention is related to the use of liquid, branch-chained fatty acid esters or hydrocarbons with about 20 to 30 C-atoms in the entire molecule as a surface analgesic and antiphlogistic, as well as the use of triglycerides of saturated fatty acids having 8 to 14 carbon atoms for such purposes.

14 Claims, No Drawings

SURFACE ANALGESIC AND ANTIPHLOGISTIC

BACKGROUND OF THE INVENTION

The invention relates to the use of liquid fatty acid esters or liquid hydrocarbons as surface analgesics and antiphlogistics.

A great number of analgesic or inflammation surpressing active materials for use on body surfaces are known, especially in the opthalmology. Most of these materials are organic, nitrogen containing compounds, which as bases are relatively inferior water-insolubles and which, therefore, are used either as free bases in an oily solution or in the form of salts in an aqueous solution. The oily solutions customarily employed for the free bases are normally sterilized, vegetable oils, which, however, exhibit the disadvantge that they, for example, build an oily film on the mucous membrane of the eye which most of the patients consider unpleasant.

Aqueous solutions, on the other hand, have the disadvantage of affecting the mucous membrane environment adversely by repeated use because they result in a change of the mucous membrane's osmotic conditions.

Thus, there is still a need for an oily carrier material for remedies used on mucous membranes, which does not have the disadvantages of the oily carriers employed until now and which especially does not result in injury to the visual faculty and give the patients unpleasant sensations when it is used in the field of ophthalmology.

SUMMARY OF THE INVENTION

In light of the consideration that an oily liquid must be especially suited as a carrier if it corresponds to the human skin fat or related fats or exhibits a part of the essential materials contained in these fats, so-called synthetic uropygial gland oils were analyzed with regard to their suitability as carries by application to the mucous membranes. Completely unexpected it was determined that these in and by themselves known compounds did not only show distinct suitability as carriers but revealed themselves as having an analgesic and antiphlogistic effect on mucous membranes.

Hence the invention relates to the use of these so-called synthetic uropygial gland oils as a surface analgesic and antiphlogistic.

In search for materials that occur naturally and are similar to the human skin fat in their sphere of effect the uropygial gland oil of the waterfowl was analyzed in detail at an early stage. The chemical analysis of the natural uropygial gland oil showed, as a distinct characteristic, presence of higher portions of essentially completely saturated, branch-chained fatty acid esters, having a total number of C-atoms of about 30. The uropygial gland oil makes it possible for the birds, when it is applied to the skin and feathers in a thin layer, to maintain their body temperature and prevent water from wetting the feathers. These characteristics have resulted in corresponding synthetic compounds already having been used for a long time in cosmetics as salve bases or salve additions because the branch-chained fatty acid esters distinguish themselves by having a special spreading ability and being without occlusive effect. Because the healthy skin continuously releases steam and carbon dioxide to the environment, a reduction of the wate evaporation results in a high water percentage and heat stagnation; this phenomenon, characterized as occlusion, furthermore results in an increase of the number of germs on the skin or mucous membrane surface and a qualitative change in the skin flora.

In addition, it was already known that the effect of the natural mucous membrane oil can be achieved not only with the help of branch-chained fatty acid esters, but also by using branch-chained essentially saturated hydrocarbons. For example squalene, the saturated compound corresponding to the natural squalene, or for example also completely synthetically produced compounds as polyisobutylenes, having a total chain length of approximately 20 to 30 C-atoms or a little more, belong to these long-chained, saturated hydrocarbons. The synthetic mucous membrane oils have been used in cosmetics and recently also to clean oil soiled waterbirds because it has been determined that the synthetic oils are capable of functionally substituting for the natural feather fat of the waterbirds after the soiled animals have been cleaned with tensides.

The inherent analgesic and antiphlogistic activity on body surfaces, determined by this time by the carrier experiment, was a complete surprise and as of now cannot be explained scientifically without ambiguity because in and by themselves no analgesic active materials are known to exhibit any structural similarity.

In terms of the so-called synthetic mucous membrane oils, it is chemically a matter of either compounds of relatively long-chained, branched carboxylic acids, as for example 2-ethyl hexanoic acid, with linear chain or branched alcohols with about 16-20 C-atoms, or essentially saturated branch-chained hydrocarbon as, for example, squalenes or hydrogenated polyisobutylenes. Because the synthesis does not begin with pure fractionations, compounds having some variation in the chain length are normally present; very small portions of unsaturated compounds can also be at hand. The chemical-physical reference numbers range within the following area: acid number under 1, the saponification number by the esters around 130-160, by the hydrocarbons under 1, hydroxyl number under 1; iodine number by the esters under 1 and under 2 by the hydrocarbons. Oils of this type are sold, for example, by the BASF company under the name of "Luvitol" and by the Dragoco company under the name of "PCL-liquid".

By using these compounds on body surfaces, their spreading ability, which is realted to the viscosity, is important. it was determined that it becomes a question of a viscosity of between about 20-80 mp according to the type of application, meaning that a viscosity of about 60 mp is preferred in the ophthalmology. The employed compounds can, according to the invention, be used not only as such but also as carriers for other active materials because of their additional characteristics, by which not only the activity of the active material but also the analgesic and inflammation suppressing activity of the carrier could be used. Such additional active materials are, for example, the other known analgesics, antibacterial, viricidal or antimycotic active compounds and the other sympatho- or parasympathomimetica or -lytica, which by the production of pharmaceutical preparations preferably are prepared as bases or in the form of oil free salts.

It has also been determined that synthetic triglycerides, which essentially are built of saturated fatty acids with around 8-14 C-atoms in a linear or branched chain can be used for the purpose indicated. Such fats are liquid and also occur naturally in small amounts in the skin fat or the mucous fat. Today these are usually obtained synthetically by esterification of glycerine with acid fractionates from caprylic to myristic acids and possibly the corresponding branch-chained acids. The entire molecule usually contains around 30 C-atoms, leaving the possibility open for variations up and down. Combinations of such triglycerides have so far been used in cosmetics as salve bases due to their spreading ability because they distinguish themselves as the fatty acid esters and hydrocarbons discussed in the parent patent not only by good spreading ability but also by an absence of occlusive activity.

The chemical-physical compounds correspond to the ones described above with the exception of the saponification number, which naturally lies higher and can range in the area of about 320-360.

In the following the invention is explained further with the help of examples.

DETAILED DESCRIPTION

Example 1

Patients with acute chemical or physical injury to the cornea caused by tear gas, metallic foreign substances, etc. had a drop of the fatty acid ester, used according to the invention, dropped into the injured eye. Already after 1 to 2 minutes the patients subjectively reported a soothing of the pain or no pain, which on the average lasted 1–4, or even up to a maximum of 12 hours. It was also surprisingly determined that an accelerated recovery without antibiotics or cordisone occurred. The average treatment period lasted 1 to 5 days, according to the extent and depth of the injury.

Example 2

Different patient groups with cornea oedema, cornea ulcer, and cornea -or conjuctivital scars following, for example, herpes infections were treated according to Example 1. An inflammation suppressing, antioedematic activity could be determined already after a treatment period of a few days and the recovery occurred in all cases without complications or additional medicaments.

Example 3

Patients experiencing difficulties by wearing soft or hard contact lenses of all types, which at the present time had already suffered subjectively from pain sensations for a long time, were treated as stated. Also in these cases the analgesic activity occurred within a short time and inflammation influenced symptoms decreased shortly.

I claim:

1. A process comprising externally applying to a patient in need of a surface analgesic or antiphlogistic a composition consisting essentially of at least one liquid, branched chain, essentially saturated fatty acid ester or hydrocarbon having predominantly 20 to 30 carbon atoms in the molecule in an analgesically or antiphlogistically effective amount.

2. A process according to claim 1 wherein the composition consists of the fatty acid ester or hydrocarbon.

3. A process according to claim 1 wherein the compound has a viscosity of about 20 to 80 mp.

4. A process according to claim 1 wherein the compounds are liquid hydrocarbons.

5. A process according to claim 4 wherein the hydrocarbons are squalene or polyisobutylenes.

6. A process according to claim 1 wherein the compounds are saturated fatty acid esters.

7. A process according to claim 1 wherein the compounds are glycerides.

8. A process according to claim 1 wherein one drop of the composition is applied to the eye.

9. A process according to claim 6 where the compounds are esters of a 16-20 carbon atom alcohol with 2-ethyl hexanoic acid.

10. A process comprising externally applying to a patient in need of a surface analgesic or antiphlogistic a composition consisting essentially of a liquid mixture of triglycerides of having 8 to 14 carbon atoms in an analgesically or antiphlogistically effective amount.

11. A process according to claim 10 wherein the composition consists of the triglycerides.

12. A process according to claim 10 wherein the total number of carbon atoms in the molecule is around 30.

13. A process according to claim 12 wherein the compounds have a viscosity of about 20 to 80 mp.

14. A process according to claim 10 wherein the composition consists essentially of ethyl hexanoic acid triglyceride.

* * * * *